United States Patent
Bresnick (10) Patent No.: US 10,179,129 B2
(45) Date of Patent: Jan. 15, 2019

(54) PROPHYLACTIC LEUKOTRIENE INHIBITOR AND IMPLANT DISPLACEMENT THERAPY FOR PREVENTION AND TREATMENT OF CAPSULAR CONTRACTURE IN SILICONE BREAST AUGMENTATION

(71) Applicant: Stephen David Bresnick, Encino, CA (US)

(72) Inventor: Stephen David Bresnick, Encino, CA (US)

( * ) Notice: Subject to any disclaimer, the term of this patent is extended or adjusted under 35 U.S.C. 154(b) by 0 days.

(21) Appl. No.: 15/864,580

(22) Filed: Jan. 8, 2018

(65) Prior Publication Data

US 2018/0193327 A1     Jul. 12, 2018

Related U.S. Application Data

(63) Continuation of application No. PCT/US2018/012718, filed on Jan. 6, 2018.

(60) Provisional application No. 62/443,122, filed on Jan. 6, 2017.

(51) Int. Cl.
  *A61K 31/47* (2006.01)
  *A61K 31/404* (2006.01)
  *A61F 2/12* (2006.01)

(52) U.S. Cl.
  CPC ............ *A61K 31/47* (2013.01); *A61K 31/404* (2013.01); *A61F 2/12* (2013.01)

(58) Field of Classification Search
  CPC ....... A61K 31/00; A61K 31/381; A61K 31/47
  See application file for complete search history.

(56) References Cited

U.S. PATENT DOCUMENTS

| 5,759,204 A * | 6/1998 | Seare, Jr. ................. | A61F 2/12 623/11.11 |
|---|---|---|---|
| 2003/0162828 A1* | 8/2003 | Schlesinger ........... | A61K 31/00 514/443 |
| 2013/0079348 A1* | 3/2013 | Velicelebi ............ | C07D 333/38 514/249 |

OTHER PUBLICATIONS

Dembny Jun. 2014 (webpage article 'Breast Implant Displacement Exercises'. Downloaded from the website on Mar. 8, 2018).*

* cited by examiner

*Primary Examiner* — Savitha M Rao
(74) *Attorney, Agent, or Firm* — Polsinelli PC (57) ABSTRACT

A method of treating or preventing capsular contracture in a patient resulting from surgical insertion of a silicone breast implant in a surgically created implant pocket. The method includes administering to the patient a therapeutically effective amount of a leukotriene receptor antagonist prior to the formation of a capsular contracture in the patient. The method further includes administering a therapeutically effective amount of displacement of the breast implant within the surgically created implant pocket, the therapeutically effective amount of displacement of the breast implant being administered post-surgically but prior to the formation of a capsular contracture in the patient.

17 Claims, 4 Drawing Sheets

PROPHYLACTIC LEUKOTRIENE INHIBITOR AND IMPLANT DISPLACEMENT THERAPY FOR PREVENTION AND TREATMENT OF CAPSULAR CONTRACTURE IN SILICONE BREAST AUGMENTATION

CROSS-REFERENCE TO RELATED APPLICATIONS

This application is a continuation of International Application No. PCT/US18/12718, entitled "Prophylactic Leukotriene Inhibitor and Implant Displacement Therapy for Prevention and Treatment of Capsular Contracture in Silicone Breast Augmentation," filed on Jan. 6, 2018, which claims the benefit of U.S. Provisional Application No. 62/443,122, entitled "Prophylactic Leukotriene Inhibitor Therapy for Reduction of Capsular Contracture in Primary Silicone Breast Augmentation," filed on Jan. 6, 2017. Both International Application No. PCT/US18/12718 and U.S. Provisional Application No. 62/443,122 are incorporated by reference in their entirety, for all purposes, herein.

FIELD OF TECHNOLOGY

The present disclosure is directed to the treatment of scarring resulting from silicone breast augmentation surgery. The present disclosure is further directed to a method of prophylactic leukotriene inhibitor therapy and implant displacement therapy for the reduction of capsular contracture in conjunction with silicone breast augmentation surgery.

BACKGROUND

Capsular contracture remains the most common complication of aesthetic breast augmentation despite advances in the understanding of the biological processes which appear to be involved. The role of biofilms in capsular contracture has been reported extensively and is believed to play an important role in the pathogenesis of capsular contracture. Recent advances in antibiotic irrigation as well as the use of skin barriers and nipple shields has assisted in the reduction of capsular contracture. Form stable implant studies with textured devices have also shown lower capsular contracture rates compared to smooth round devices. Yet, despite these advances, a significant number of women develop capsular contracture following breast augmentation and require revisional surgery or live with discomfort, deformity, or suboptimal results.

Three cysteinyl leukotrienes, LTC4, LTD4, and LTE4 are products of arachidonic acid metabolism and are released from cells associated with the inflammatory response. These compounds bind to cysteinyl leukotriene receptors which are found on smooth muscle cells and inflammatory cells. When leukotrienes bind to the cysteinyl leukotriene receptor, multiple effects including cellular contraction, edema, and altered cellular activity associated with inflammation may occur. Montelukast (Singulair) inhibits the actions of one leukotriene, LTD4, at the cysteinyl leukotriene receptor. Zafirlukast (Accolate) is a competitive receptor antagonist for leukotrienes, and is known to antagonize the contractile activity of three different leukotrienes, including LTC4, LTD4, and LTE4. These leukotrienes are associated with the inflammatory process, smooth muscle and cellular contraction. Zafirlukast (Accolate) competitively inhibits three different leukotrienes, rather than the one leukotriene inhibited by Montelukast (Singulair).

The use of leukotriene inhibitors for the treatment of capsular contracture was reported as early as 2002, and multiple studies have shown benefits in softening breasts and reducing the severity of capsular contracture with either Singulair or Accolate. However, the prophylactic use of these medications immediately postoperatively, and before there is any evidence of capsular contracture in the patient is unknown. Additionally, methods for the effective prophylactic treatment of patients undergoing revisional surgery for capsular contracture are unknown. Currently, there is no clear standard of care for the use of these off-label medications, and little information is available regarding effective methods in their use in treating and preventing capsular contracture in patients. Accordingly, improved methods for the prevention and treatment of capsular contracture in patients is desirable.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

As used herein, the terms "perioperative" or "perioperatively," in all its forms, refer to the period beginning two weeks prior to the breast augmentation surgery or breast augmentation revision surgery and ending two weeks following completion of the surgery, encompassing any subset therebetween. Accordingly, perioperative administration includes administration any time during the perioperative period and may continue beyond the perioperative period until the leukotriene receptor antagonist therapy is completed.

The present disclosure provides methods for the treatment and prevention of capsular contracture in patients resulting from breast augmentation surgery as well as the recurrence of capsular contracture in patients undergoing capsulectomy and silicone breast implant replacement surgery. It has been unexpectedly found that perioperative administration of leukotriene receptor antagonist therapy in combination with implant displacement therapy, according to the presently disclosed methods, is especially effective in the prevention and treatment of capsular contracture. It has further been unexpectedly found that the presently disclosed methods are particularly effective in the prevention and treatment of capsular contracture in patients undergoing capsulectomy and implant replacement surgery.

According to at least one aspect of the present disclosure, a method of treating or preventing capsular contracture in a patient resulting from surgical insertion of a silicone breast implant in a surgically created implant pocket is provided. The method includes administering to the patient a therapeutically effective amount of a leukotriene receptor antagonist prior to the formation of a capsular contracture in the patient. The method also includes administering a therapeutically effective amount of displacement of the breast implant within the surgically created implant pocket. The therapeutically effective amount of displacement of the breast implant is administered post-surgically but prior to the formation of capsular contracture in the patient. In at least some instances, the leukotriene receptor antagonist is administered perioperatively and continued for at least three months following surgical insertion of the silicone breast implant in the surgically created implant pocket. The leukotriene receptor antagonist therapy may be first administered, for example, two weeks, or ten days, or one week, or 48 hours, or 24 hours prior to surgical insertion of the silicone breast implant into the surgically created implant pocket in the patient. In other instances, the leukotriene receptor antagonist therapy may be first administered 24 hours, or 48 hours, or one week, or ten days, or two weeks following surgical implantation of the implant. In all cases, once the leukotriene receptor antagonist administration is initiated, administration may be continued daily until at least three months following surgical implantation of the implant. In some cases, the leukotriene receptor antagonist may be montelukast or zafirlukast. In cases in which the leukotriene receptor antagonist is zafirlukast, the therapeutically effective amount may be 20 mg/bid administered orally. In instances in which montelukast is the leukotriene receptor antagonist administered, the therapeutically effective amount may be 10 mg/day administered orally. In at least some cases, the patient may also be administered antibiotic-betadine irrigation.

In at least some instances, the therapeutically effective amount of displacement may include upward displacement, upward and downward displacement, and inward-outward displacement or outward-inward displacement. At least ten displacement repetitions may be administered at least three times daily. In some cases, the therapeutically effective amount of displacement includes displacing the implant from its resting position in the implant pocket in an upward direction and extending to the upper-most limit of implant movement or to the limits of the surgically-created pocket. In other cases, the therapeutically effective amount of displacement includes displacing the implant in both an upward and downward direction in which the displacement is administered as at least ten displacement repetitions administered at least three times daily. In some instances, the therapeutically effective amount of displacement includes displacing the implant from an inner portion of a breast to an outer portion of the breast or displacing the implant from the outer portion of the breast to the inner portion. In such instances, the displacement may be administered as at least ten displacement repetitions administered at least three times daily.

In at least some instances, the method may further include monitoring transaminase levels in the blood of the patient and determining whether to continue leukotriene receptor antagonist therapy based on the monitoring of transaminase levels. In such instances, the leukotriene receptor antagonist may be administered until either the patient exhibits a Baker I or Baker II grade breast for at least three months following insertion of a silicone implant in a surgically created implant pocket in that breast or until the patient exhibits blood levels of transaminase that are elevated beyond safe limits.

According to at least one aspect of the present disclosure, a method of treating capsular contracture in a patient undergoing capsulectomy and silicone breast implant replacement surgery is provided. The method includes perioperative administration to the patient of a therapeutically effective amount of a leukotriene receptor antagonist. In at least some instances, the leukotriene receptor antagonist is administered for at least three months following surgical insertion of the silicone breast implant in the surgically created implant pocket. The leukotriene receptor antagonist therapy may be first administered, for example, two weeks, or ten days, or one week, or 48 hours, or 24 hours prior to surgical insertion of the silicone breast implant into the surgically created implant pocket in the patient. In other instances, the leukotriene receptor antagonist therapy may be first administered 24 hours, or 48 hours, or one week, or ten days, or two weeks following surgical implantation of the implant. In all cases, once the leukotriene receptor antagonist administration is initiated, administration may be continued daily until at least three months following surgical implantation of the implant. In some cases, the leukotriene receptor antagonist may be montelukast or zafirlukast. In cases in which the leukotriene receptor antagonist is zafirlukast, the therapeutically effective amount may be 20 mg/bid administered orally. In instances in which montelukast is the leukotriene receptor antagonist administered, the therapeutically effective amount may be 10 mg/day administered orally. In at least some cases, the patient may also be administered antibiotic-betadine irrigation. In some instances, the method may also include administering a therapeutically effective amount of displacement of the breast implant within the surgically created implant pocket. In such cases, the displacement of the breast implant may be administered to the patient post-surgically but prior to the recurrence of a capsular contracture in the patient.

According to at least one aspect of the present disclosure, a method of treating or preventing recurrence of capsular contracture in a patient undergoing capsulectomy and silicone breast implant replacement surgery is provided. The method includes perioperative administration to the patient of a therapeutically effective amount of a leukotriene receptor antagonist. The method also includes administering a therapeutically effective amount of displacement of the breast implant within the surgically created implant pocket. The displacement of the breast implant is administered to the patient post-surgically but prior to the recurrence of a capsular contracture in the patient. In at least some instances, the leukotriene receptor antagonist is administered for at least three months following surgical insertion of the silicone breast implant in the surgically created implant pocket.

According to at least one other aspect of the present disclosure, a method of treating capsular contracture associated with a silicone breast implant in a patient is provided. The method includes removing the silicone implant from a surgically created implant pocket in the patient. The method further includes performing a capsulectomy to remove the scar tissue surrounding the implant pocket and inserting a replacement silicone implant into the implant pocket. The method also includes administering to the patient a therapeutically effective amount of a leukotriene receptor antagonist prior to the formation of a capsular contracture associated with the replacement silicone implant in the patient. The method also includes performing displacement of the replacement silicone implant within the surgically created implant pocket. The displacement of the breast implant is performed post-surgically but prior to the formation of capsular contracture in the patient. In at least some instances, the leukotriene receptor antagonist is administered perioperatively and continued for at least three months following surgical insertion of the silicone breast implant in the surgically created implant pocket.

According to at least one other aspect of the present disclosure, a method of treating recurrence of capsular contracture in a patient following silicone implant replacement for Baker grade III or grade IV capsular contracture is provided. The method includes removing the silicone implant from a surgically created implant pocket in the patient. The method further includes performing a capsulectomy to remove the scar tissue surrounding the implant pocket and inserting a replacement silicone implant into the implant pocket. The method also includes administering to the patient a therapeutically effective amount of a leukotriene receptor antagonist prior to the formation of a capsular contracture associated with the replacement silicone implant in the patient. The method also includes performing displacement of the replacement silicone implant within the surgically created implant pocket. The displacement of the breast implant is performed post-surgically but prior to the formation of capsular contracture in the patient. In at least some instances, the leukotriene receptor antagonist is administered perioperatively and continued for at least three months following surgical insertion of the silicone breast implant in the surgically created implant pocket.

According to at least one aspect of the present disclosure, the presently disclosed technique may be applicable to reducing scarring associated with surgically inserted implants in other tissues or organs of a patient.

Figure 1:
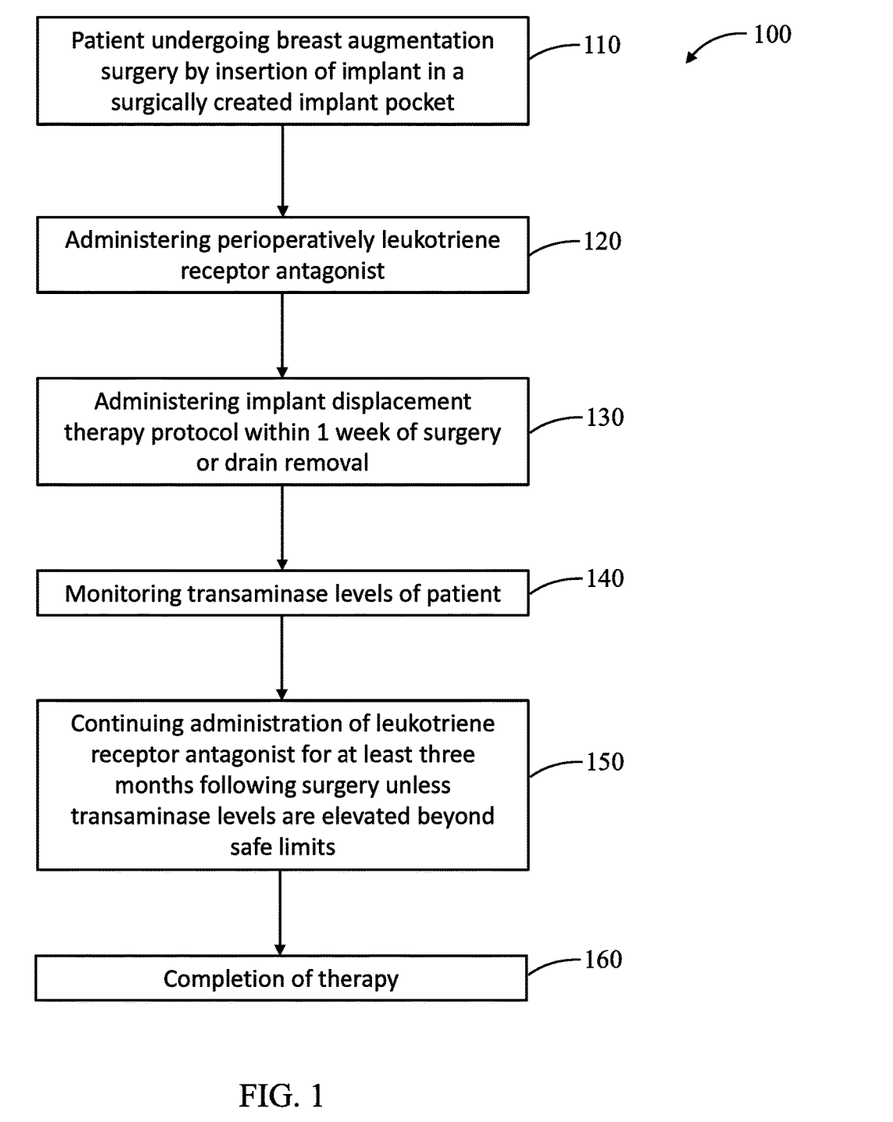
FIG. 1 is a flowchart describing a method of treating or preventing capsular contracture in a patient resulting from breast augmentation surgery, according to an exemplary embodiment of the present disclosure.

FIG. 1 depicts a flowchart describing a method of treating or preventing capsular contracture in a patient resulting from surgical insertion of a silicone breast implant in a surgically created implant pocket, according to an exemplary embodiment of the present disclosure. The example method shown in FIG. 1 is provided by way of an example, as there are a variety of ways to carry out the method. Each block shown in FIG. 1 represents one or more processes or methods carried out in the example method shown in FIG. 1. Furthermore, the illustrated order of blocks is illustrative only and the order of the blocks can change according to the present disclosure. Additional blocks can be added or fewer blocks can be utilized, without departing from this disclosure.

Method 100 depicted in FIG. 1 is an example method, according to an example embodiment of the present disclosure. The method 100 depicted in FIG. 1 is just an example method and can be adopted to various operating environments by adding or removing one or more blocks. The example method 100 can begin at block 110. At block 110, a patient undergoing breast augmentation surgery is provided. The breast augmentation surgery involves surgery by insertion of an implant in a surgically created implant pocket. In at least some instances, the implant may be a silicone implant. In some cases, the implant may be a smooth silicone implant. In some instances, block 110 may include performing a breast augmentation surgery by inserting an implant into a surgically created implant pocket. However, the presently disclosed methods and techniques are not limited to those methods including a step involving performing the breast augmentation surgery.

At block 120, method 100 includes administering leukotriene receptor antagonist to the patient perioperatively and prior to the formation of a capsular contracture in the patient. The leukotriene receptor antagonist therapy may be first administered, for example, two weeks, or ten days, or one week, or 48 hours, or 24 hours prior to surgical insertion of the silicone breast implant into the surgically created implant pocket in the patient. In other instances, the leukotriene receptor antagonist therapy may be first administered 24 hours, or 48 hours, or one week, or ten days, or two weeks following surgical implantation of the implant. In all cases, once the leukotriene receptor antagonist administration is initiated, administration may be continued daily until the completion of the therapy at block 160. In some cases, the leukotriene receptor antagonist may be montelukast or zafirlukast. In cases in which the administered leukotriene receptor antagonist is zafirlukast, administration may include 20 mg/bid administered orally. In instances in which montelukast is the administered leukotriene receptor antagonist, administration may include 10 mg/day administered orally.

At block 130, implant displacement therapy protocol is initiated within one week of surgery or within one week of drain removal if a drain was used. The implant displacement therapy protocol may include any of the implant displacement therapeutic techniques disclosed herein. The implant displacement therapy protocol may include, for example, administration of at least ten displacement repetitions administered at least three times daily. After initiation of the implant displacement therapy protocol at block 130, the implant displacement therapy is continued until completion of the therapy at block 160 and/or for at least 3 months following surgical implantation of the implant in the surgically created implant pocket.

At block 140, transaminase levels in the blood of the patient are monitored in order to determine whether it is safe to continue leukotriene receptor antagonist therapy in the patient. At block 150, the leukotriene receptor antagonist administration is continued for at least three months following surgery unless the monitored transaminase levels are elevated beyond safe limits. At block 160, the leukotriene receptor antagonist therapy and the implant displacement therapy protocol are completed upon determination that the surgically implanted breast in the patient is characterized by a Baker grade I or grade II soft breasts at a period of three months following surgery or later.

Figure 2:
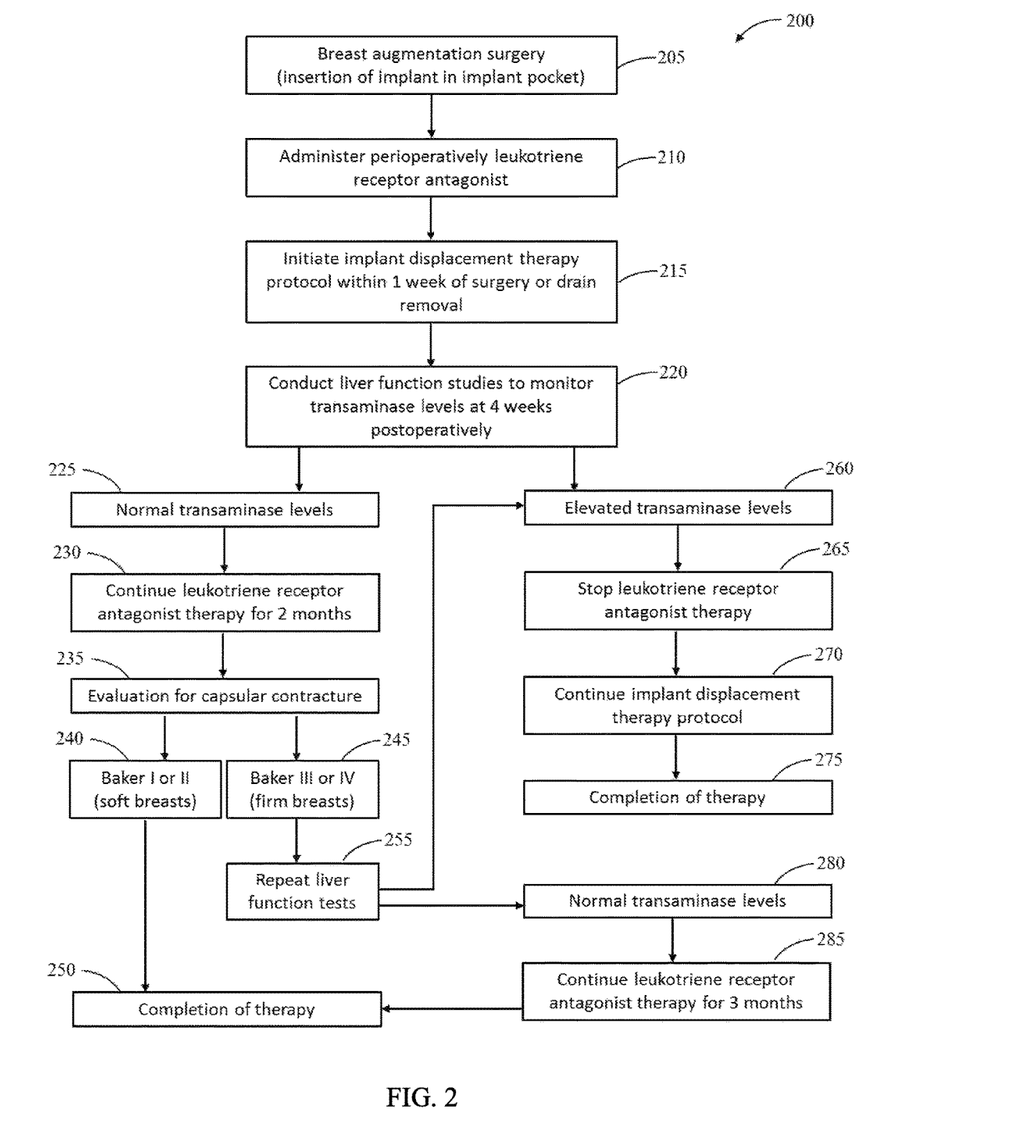
FIG. 2 is a flowchart describing a method of treating or preventing capsular contracture in a patient resulting from breast augmentation surgery including a specific transaminase monitoring protocol, according to an exemplary embodiment of the present disclosure.

FIG. 2 depicts a flowchart describing a method of treating or preventing capsular contracture in a patient resulting from surgical insertion of a silicone breast implant in a surgically created implant pocket that includes a specific transaminase monitoring protocol, according to an exemplary embodiment of the present disclosure. The example method shown in FIG. 2 is provided by way of an example, as there are a variety of ways to carry out the method. Each block shown in FIG. 2 represents one or more processes or methods carried out in the example method shown in FIG. 2. Furthermore, the illustrated order of blocks is illustrative only and the order of the blocks can change according to the present disclosure. Additional blocks can be added or fewer blocks can be utilized, without departing from this disclosure.

Method 200 depicted in FIG. 2 is an example method, according to an example embodiment of the present disclosure. The method 200 depicted in FIG. 2 is just an example method and can be adopted to various operating environments by adding or removing one or more blocks. The example method 200 can begin at block 205. At block 205, a patient undergoing breast augmentation surgery is provided. The breast augmentation surgery involves surgery by insertion of an implant in a surgically created implant pocket. In at least some instances, the implant may be a silicone implant. In some cases, the implant may be a smooth silicone implant. In some instances, block 205 may include performing a breast augmentation surgery by inserting an implant into a surgically created implant pocket. However, the presently disclosed methods and techniques are not limited to those methods including a step involving performing the breast augmentation surgery.

At block 210, method 200 includes administering leukotriene receptor antagonist to the patient perioperatively and prior to the formation of a capsular contracture in the patient. The leukotriene receptor antagonist therapy may be first administered, for example, two weeks, or ten days, or one week, or 48 hours, or 24 hours prior to surgical insertion of the silicone breast implant into the surgically created implant pocket in the patient. In other instances, the leukotriene receptor antagonist therapy may be first administered 24 hours, or 48 hours, or one week, or ten days, or two weeks following surgical implantation of the implant. In all cases, once the leukotriene receptor antagonist administration is initiated, administration may be continued daily until the completion of the therapy at block 250. In some cases, the leukotriene receptor antagonist may be montelukast or zafirlukast. In cases in which the administered leukotriene receptor antagonist is zafirlukast, administration may include 20 mg/bid administered orally. In instances in which montelukast is the administered leukotriene receptor antagonist, administration may include 10 mg/day administered orally.

At block 215, implant displacement therapy protocol is initiated within one week of surgery or within one week of drain removal if a drain was used. The implant displacement therapy protocol may include any of the implant displacement therapeutic techniques disclosed herein. The implant displacement therapy protocol may include, for example, administration of at least ten displacement repetitions administered at least three times daily. After initiation of the implant displacement therapy protocol at block 215, the implant displacement therapy is continued until completion of the therapy at block 250 and/or for at least 3 months following surgical implantation of the implant in the surgically created implant pocket.

At block 220, liver function studies are conducted at four weeks following surgical implantation of the implant in order to monitor transaminase levels in the blood of the patient. A determination is made at block 220 as to whether the transaminase levels in the patient are normal or within safe limits (block 225) or whether the transaminase levels are elevated (block 260). If transaminase levels are determined to be normal (block 225), leukotriene receptor antagonist therapy is continued at block 230 for an additional two months. At block 235, the patient is evaluated for capsular contracture at the end of three months following surgical implantation of the implant. If the patient is determined at block 240 to have Baker grade I or grade II breasts, corresponding to substantially capsular contracture-free soft breasts, the therapy is completed at block 250. If, however, the patient is determined to have Baker grade III or grade IV breasts at block 245, corresponding to an indication of capsular contracture and firm breasts, the liver function tests are repeated at block 255. If the patient is determined to have normal or safe transaminase levels at block 280, leukotriene receptor antagonist therapy is continued for an additional three months at block 285 until completion of therapy at block 250. If, at block 255, the patient is determined to have elevated transaminase levels (block 260), leukotriene receptor antagonist therapy is stopped at block 265. In such cases, the implant displacement therapy protocol is continued at block 270 until the completion of therapy at block 275.

Figure 3:
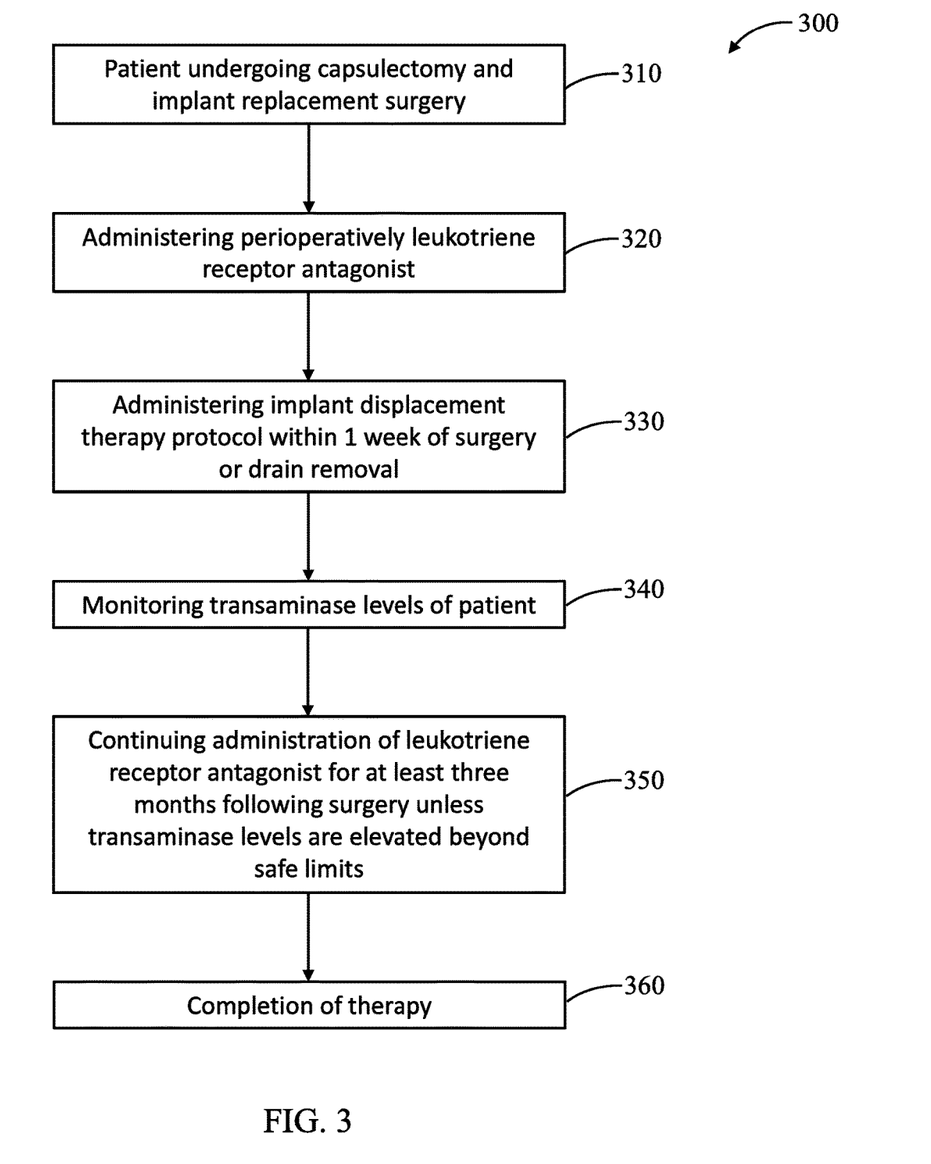
FIG. 3 is a flowchart describing a method of treating or preventing the recurrence of capsular contracture in a patient undergoing capsulectomy and silicone implant replacement surgery, according to an exemplary embodiment of the present disclosure.

FIG. 3 depicts a flowchart describing a method of treating or preventing recurrence of capsular contracture in a patient undergoing capsulectomy and silicone breast implant replacement surgery, according to an exemplary embodiment of the present disclosure. The example method shown in FIG. 3 is provided by way of an example, as there are a variety of ways to carry out the method. Each block shown in FIG. 3 represents one or more processes or methods carried out in the example method shown in FIG. 3. Furthermore, the illustrated order of blocks is illustrative only and the order of the blocks can change according to the present disclosure. Additional blocks can be added or fewer blocks can be utilized, without departing from this disclosure.

Method 300 depicted in FIG. 3 is an example method, according to an example embodiment of the present disclosure. The method 300 depicted in FIG. 3 is just an example method and can be adopted to various operating environments by adding or removing one or more blocks. The example method 300 can begin at block 310. At block 310, a patient undergoing capsulectomy and silicone breast implant replacement surgery is provided. The silicone breast implant replacement surgery involves removal of the silicone implant from a surgically created implant pocket in the patient and a capsulectomy to remove the scar tissue surrounding the implant pocket, followed by insertion of the replacement silicone implant in the implant pocket. In at least some instances, the implant may be a silicone implant. In some cases, the implant may be a smooth silicone implant. In some instances, block 310 may include performing a revisional breast augmentation surgery by removing the silicone implant from a surgically created implant pocket in the patient and performing a capsulectomy to remove the scar tissue surrounding the implant pocket, followed by inserting a replacement silicone implant into the implant pocket. However, the presently disclosed methods and techniques are not limited to those methods including a step involving performing the revisional breast augmentation surgery, capsulectomy, or silicone breast implant replacement surgery.

At block 320, method 300 further includes administering leukotriene receptor antagonist to the patient perioperatively and prior to the recurrence of a capsular contracture in the patient. The leukotriene receptor antagonist therapy may be first administered, for example, two weeks, or ten days, or one week, or 48 hours, or 24 hours prior to surgical insertion of the silicone breast implant into the surgically created implant pocket in the patient. In other instances, the leukotriene receptor antagonist therapy may be first administered 24 hours, or 48 hours, or one week, or ten days, or two weeks following surgical implantation of the implant. In all cases, once the leukotriene receptor antagonist administration is initiated, administration may be continued daily until the completion of the therapy at block 360. In some cases, the leukotriene receptor antagonist may be montelukast or zafirlukast. In cases in which the administered leukotriene receptor antagonist is zafirlukast, administration may include 20 mg/bid administered orally. In instances in which montelukast is the administered leukotriene receptor antagonist, administration may include 10 mg/day administered orally.

At block 330, implant displacement therapy protocol is initiated within one week of surgery or within one week of drain removal if a drain was used. The implant displacement therapy protocol may include any of the implant displacement therapeutic techniques disclosed herein. The implant displacement therapy protocol may include, for example, administration of at least ten displacement repetitions administered at least three times daily. After initiation of the implant displacement therapy protocol at block 330, the implant displacement therapy is continued until completion of the therapy at block 360 and/or for at least 3 months following surgical implantation of the replacement implant in the surgically created implant pocket.

At block 340, transaminase levels in the blood of the patient are monitored in order to determine whether it is safe to continue leukotriene receptor antagonist therapy in the patient. At block 350, the leukotriene receptor antagonist administration is continued for at least three months following the implant replacement surgery unless the monitored transaminase levels are elevated beyond safe limits. At block 360, the leukotriene receptor antagonist therapy and the implant displacement therapy protocol are completed upon determination that the surgically implanted breast in the patient is characterized by a Baker grade I or grade II soft breasts at a period of three months following surgery or later.

Figure 4:
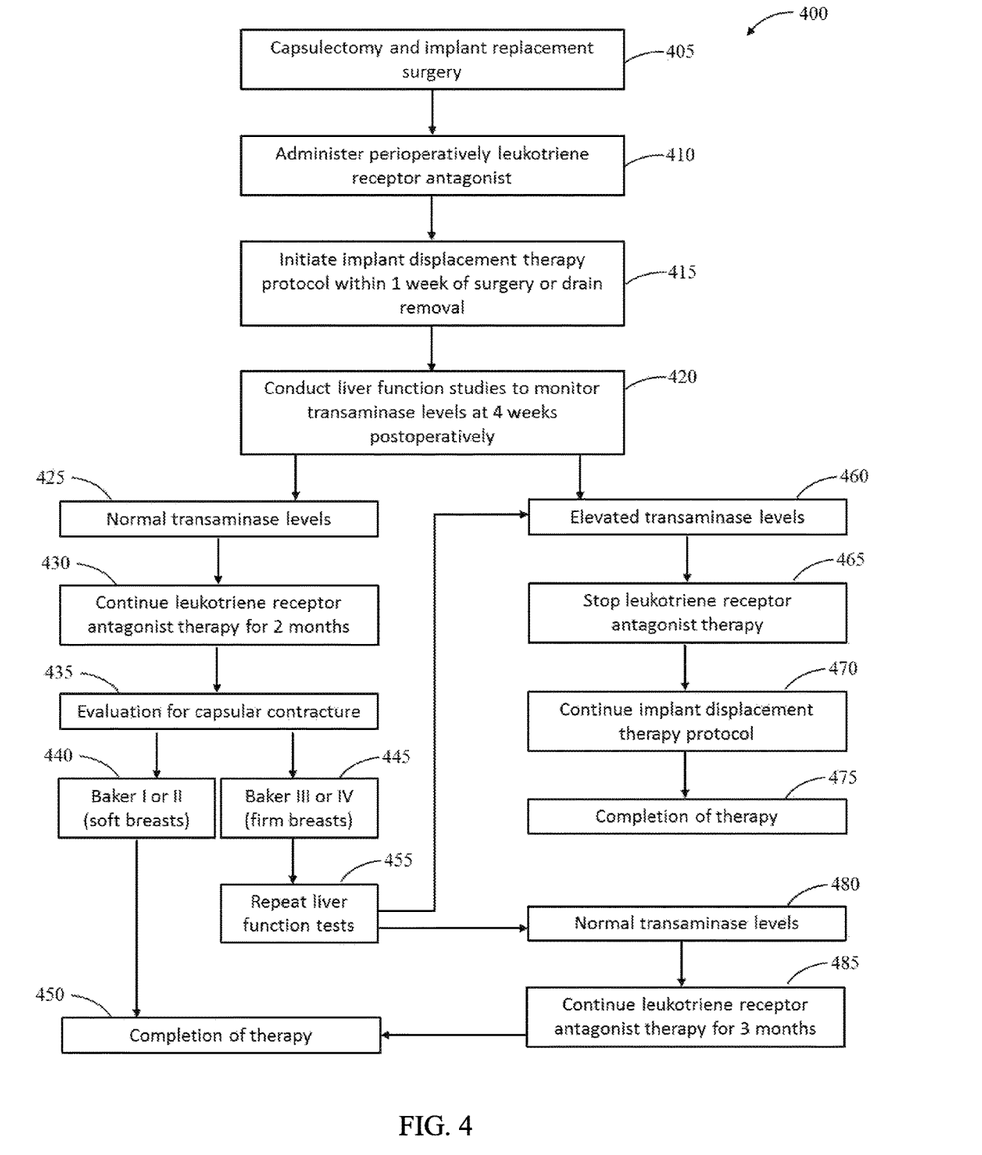
FIG. 4 is a flowchart describing a method of treating or preventing the recurrence of capsular contracture in a patient undergoing capsulectomy and silicone implant replacement surgery including a specific transaminase monitoring protocol, according to an exemplary embodiment of the present disclosure.

FIG. 4 depicts a flowchart describing a method of treating or preventing the recurrence of capsular contracture in a patient undergoing capsulectomy and silicone implant replacement surgery including a specific transaminase monitoring protocol, according to an exemplary embodiment of the present disclosure. The example method shown in FIG. 4 is provided by way of an example, as there are a variety of ways to carry out the method. Each block shown in FIG. 4 represents one or more processes or methods carried out in the example method shown in FIG. 4. Furthermore, the illustrated order of blocks is illustrative only and the order of the blocks can change according to the present disclosure. Additional blocks can be added or fewer blocks can be utilized, without departing from this disclosure.

Method 400 depicted in FIG. 4 is an example method, according to an example embodiment of the present disclosure. The method 400 depicted in FIG. 4 is just an example method and can be adopted to various operating environments by adding or removing one or more blocks. The example method 400 can begin at block 405. At block 405, a patient undergoing capsulectomy and silicone breast implant replacement surgery is provided. The silicone breast implant replacement surgery involves removal of the silicone implant from a surgically created implant pocket in the patient and a capsulectomy to remove the scar tissue surrounding the implant pocket, followed by insertion of the replacement silicone implant in the implant pocket. In at least some instances, the implant may be a silicone implant.

In some cases, the implant may be a smooth silicone implant. In some instances, block 405 may include performing a revisional breast augmentation surgery by removing the silicone implant from a surgically created implant pocket in the patient and performing a capsulectomy to remove the scar tissue surrounding the implant pocket, followed by inserting a replacement silicone implant into the implant pocket. However, the presently disclosed methods and techniques are not limited to those methods including a step involving performing the revisional breast augmentation surgery, capsulectomy, or silicone breast implant replacement surgery.

At block 410, method 400 includes administering leukotriene receptor antagonist to the patient perioperatively and prior to the recurrence of a capsular contracture in the patient. The leukotriene receptor antagonist therapy may be first administered, for example, two weeks, or ten days, or one week, or 48 hours, or 24 hours prior to surgical insertion of the replacement silicone breast implant into the surgically created implant pocket in the patient. In other instances, the leukotriene receptor antagonist therapy may be first administered 24 hours, or 48 hours, or one week, or ten days, or two weeks following surgical implantation of the replacement implant. In all cases, once the leukotriene receptor antagonist administration is initiated, administration may be continued daily until the completion of the therapy at block 450. In some cases, the leukotriene receptor antagonist may be montelukast or zafirlukast. In cases in which the administered leukotriene receptor antagonist is zafirlukast, administration may include 20 mg/bid administered orally. In instances in which montelukast is the administered leukotriene receptor antagonist, administration may include 10 mg/day administered orally.

At block 415, implant displacement therapy protocol is initiated within one week of surgery or within one week of drain removal if a drain was used. The implant displacement therapy protocol may include any of the implant displacement therapeutic techniques disclosed herein. The implant displacement therapy protocol may include, for example, administration of at least ten displacement repetitions administered at least three times daily. After initiation of the implant displacement therapy protocol at block 415, the implant displacement therapy is continued until completion of the therapy at block 450 and/or for at least 3 months following surgical implantation of the replacement implant in the surgically created implant pocket.

At block 420, liver function studies are conducted at four weeks following surgical implantation of the implant in order to monitor transaminase levels in the blood of the patient. A determination is made at block 420 as to whether the transaminase levels in the patient are normal or within safe limits (block 425) or whether the transaminase levels are elevated (block 460). If transaminase levels are determined to be normal (block 425), leukotriene receptor antagonist therapy is continued at block 430 for an additional two months. At block 435, the patient is evaluated for capsular contracture at the end of three months following surgical implantation of the replacement implant. If the patient is determined at block 440 to have Baker grade I or grade II breasts, corresponding to substantially capsular contracture-free soft breasts, the therapy is completed at block 450. If, however, the patient is determined to have Baker grade III or grade IV breasts at block 445, corresponding to an indication of capsular contracture and firm breasts, the liver function tests are repeated at block 455. If the patient is determined to have normal or safe transaminase levels at block 480, leukotriene receptor antagonist therapy is continued for an additional three months at block 485 until completion of therapy at block 250. If, at block 455, the patient is determined to have elevated transaminase levels (block 260), leukotriene receptor antagonist therapy is stopped at block 465. In such cases, the implant displacement therapy protocol is continued at block 470 until the completion of therapy at block 475.

The implant displacement therapy protocol disclosed in FIGS. 1-4 has been found to be an important step in the presently disclosed method for treating or preventing capsular contracture in patients. In particular, displacement of the implant in the surgically created implant pocket according to the presently described techniques and method prevents contraction of the implant pocket and when performed in conjunction with the leukotriene receptor antagonist results in effective treatment or prevention of capsular contracture. These two modalities work together to reduce the incidence of capsular contracture. The leukotriene inhibitor medications effectively reduce the contraction forces within the breast pocket by blocking the inflammation-induced cellular contraction. The implant displacement therapy protocol works to mechanically maintain the pocket open and reduce the effect of contractile healing forces. It is important to begin this combination therapy prior to any clinical evidence of capsular contracture to maximize outcome and to reduce the incidence of capsular contracture. Either administration of the implant displacement therapy protocol or administration of leukotriene receptor antagonist therapy taken alone were shown in our study to have higher capsular contracture rates than the combination of leukotriene receptor antagonist therapy in conjunction with the implant displacement protocol therapy, thereby validating the benefits of combination therapy.

Breast implants are placed in a surgically created pocket beneath the breast. The pocket can be created in either a subglandular (beneath breast tissue) or subpectoral/submuscular (under pectoral muscle) plane. The implant pocket often contracts following placement of a breast implant. The early formation of scar tissue is often associated with contraction. When contraction around a breast implant occurs within the implant pocket, mobility of the implant is reduced, and the implant shape and position may become distorted. The breast often becomes abnormally firm and contracted, resulting in clinical capsular contracture. It has been unexpectedly discovered that capsular contracture may be effectively treated or prevented by the presently disclosed implant displacement therapy protocol that utilizes a specific technique to mechanically resist forces of pocket contraction by displacing the implant within the implant pocket. The technique involves up to three specific technical movements of the implant within the breast pocket. The presently disclosed implant displacement therapy protocol may be performed by a patient in need thereof, or by a physician or a massaging device.

Implant Displacement Therapy Protocol

1. Upward Displacement: This technique is designed to maintain mobility of the breast implant in the vertical dimension. The patient is instructed to displace the breast implant from its resting position in the pocket in an upward direction, extending to the upper-most limit of implant movement or the limits of the surgically-created pocket. Two options may be used for the upward displacement technique. The first technique is performed with an open hand grasping the base of the breast and compressing the thumb and forefingers together across the breast. This compressive force helps move the breast implant upwards to the extent to which the implant pocket is open. The second option for this technique is performed by placing the open hand with fingers extended at the base of the breast. The hand presses downwards and upwards on the lower breast region and displaces the implant upwards to the extent possible within the pocket. The technique can be performed by either hand on either breast. The technique is to be performed with a minimum of ten repetitions, but often more repetitions are beneficial with up to fifty repetitions utilized at least three times daily.

2. Upward and Downward Displacement: This technique is designed to encourage a full-extent of implant mobility in the vertical dimension within the pocket and to encourage breast implants to drop into the appropriate position within the pocket. This technique requires that the patient uses both hands to assist in implant displacement. In this technique, the implant is upwardly displaced with either a grasping compression by thumb and forefingers at the breast base or utilizing an open hand with fingers extended as outlined in the previous section. Once the implant is displaced upwards, the opposite hand is used to gently displace the implant downwards to the lowest position in the breast. This is done with the second hand in the open position and either grasping the upper breast with the thumb and forefingers or using an open hand and compressing the breast downwards and inwards. This technique is best performed in continuity, such that when the implant is displaced upwards, it is held in this position until it is compressed downwards by the opposite hand, with the successive repetitions being in continuity. This technique is to be performed with a minimum of ten repetitions, but often more repetitions are beneficial with up to fifty repetitions utilized at least three times daily.

3. Inward-Outward Displacement: This technique is designed to encourage a full-extent of implant mobility within the pocket, and to encourage free movement of implants in the horizontal dimension. The technique can be performed with one hand or two hands. For the one hand technique, the hand on the same side as the breast implant to be displaced, compresses the breast with the forefingers along the cleavage in an outward direction until the implant moves outward to the limits of the pocket. The opposite hand can also compress the opposite breast against the inner breast cleavage and move the implant outwards. The right hand compresses the right breast outwards and the left hand compresses the left breast outwards. Compression is then released and the implants are allowed to move back to their resting position within the pockets. Two hands can also be used in this technique to allow the simultaneous outward movement of the breast implants. The forefingers of the hands are placed in the cleavage such that the left hand compresses the left breast in an outward direction and the right hand compresses the right breast in an outward direction to the limit of the pockets. Compression is then released and the implants are allowed to move back to their resting position within the pockets.

4. Outward-Inward Displacement: This technique is designed to encourage a full-extent of implant mobility within the pocket, and to encourage optimization of cleavage and free movement of implants in the horizontal dimension. The technique can be performed with one hand or two hands. In the one hand technique, the opposite hand compresses the opposite outer breast in an inwards direction towards the cleavage. Compression is then released and the implant is allowed to move back to the resting position within the pocket. The technique is repeated for the opposite hand and breast. Two hands can also be used in this technique to allow simultaneous treatment of both breasts. The hands are crossed in front of the body, with the opposite hand placed on the outer aspect of each breast. For example, the right hand would be placed on the outer left breast and the left hand would be placed on the outer right breast. The hands are maintained in an open position and the forefingers are used to compress the implants together, moving the implants to the edge of the cleavage. Compression is then released and the implants are allowed to move back to their resting position within the pockets. This can be performed one breast at a time, or simultaneously with both breasts.

EXAMPLE 1

Treatment and Prevention of Capsular Contracture in Patients Resulting from Primary Silicone Implant Breast Augmentation A high-volume aesthetic breast practice with a single surgeon performing a standardized procedure provided an excellent opportunity to evaluate the effects of leukotriene inhibitor therapy. The author timely implemented the advances advocated by research in our specialty in regards to reduction of biofilm exposure, utilizing triple-antibiotic/betadine irrigation and the use of skin barriers/nipple shields. Yet, despite these techniques which lowered the encapsulation rates among our patients to well below national averages reported, we desired to explore the potential benefits of leukotriene therapy used prophylactically in the early postoperative period.

The study was performed with a retrospective review of 1122 consecutive women undergoing primary, silicone gel breast augmentation. Over time, the author added leukotriene inhibitor therapy to the postoperative treatment of patients. The first group of patients were treated without leukotriene therapy. Consecutive patients agreeing to the off-label use of leukotriene inhibitors were then studied. The second group of consecutive patients was offered Singulair therapy postoperatively while all other aspects of the surgical technique and care remained the same. Finally, the author offered Accolate therapy to the final group of patients undergoing breast augmentation.

All patients were between the ages of 22 and 60 years, and consented to the use of silicone gel breast implants. All patients were provided with informed consent for the use of Mentor Memory Gel silicone implants, as well as the off-label use of triple antibiotic irrigation containing betadine. In addition, a detailed informed consent was provided as well for the off-label use of either Singulair or Accolate. All patients were adequately informed of the risks, potential unknown benefits, cost, and potential side effects of leukotriene therapy with both a verbal and written consent. Patients were informed that taking leukotriene inhibitor medications was voluntary and that they could discontinue these medications at any time for any reason. In particular, patients were counseled on the potential significant risks of leukotriene inhibitors, including the uncommon risk of chemical hepatitis, liver failure, and even death, all of which were reported in Accolate FDA post-approval studies for the treatment of asthma.

Patients chose augmentation with either a periareolar or inframammary approach. Silicone breast augmentation procedures were performed using a standardized, dual plane technique. All patients were treated with preoperative intravenous antibiotics, either a one-gram dose of cephazolin or 600 mg of clindamycin, selected based on allergy profiles. Prior to insertion of implants, triple-antibioic irrigation (50,000 U bacitracin, 1 g Ancef, 80 mg gentamicin) with the addition of 50 ml of povidone-iodine in 500 ml of normal saline was utilized. All implants were placed with powerfree glove changes, and inserted through a skin barrier/nipple shield using Tegaderm dressings. The implant displacement therapy protocol was initiated on post-operative day two.

Patients that were administered Singulair were treated according to the method described in FIGS. 1 and 2 of the present disclosure. First, patients were evaluated clinically to see if they were a candidate for breast augmentation with physical examination and medical history. The medical history review included discussion and review of liver health, current medications, and potential contraindications or drug interactions with leukotriene inhibitors. Patients were then provided an informed consent for the use of Singulair, 10 mg daily. The informed consent reviewed the potential benefits and risks of this medication which is taken as an off-label indication. Breast augmentation was performed with either smooth or textured silicone or saline implants. On the day following surgery, Singulair therapy is initiated, 10 mg QD. In the first week following surgery, the implant displacement therapy protocol was begun for patients with smooth surface silicone implants. The implant displacement therapy protocol may also be performed, if indicated, for patients with mildly textured breast implants, but not with moderately textured or highly textured devices. Monitoring for side effects from Singulair was conducted by educating patients as to the common side effects and discussing with patients noted side effects. Singulair can be discontinued if the side effects are significant. At thirty days postoperatively, the softness of the breast implants as well as the implant movement and position was evaluated to determine if capsular contracture was present. Two more months of Singulair was prescribed. Following three total months of therapy, the breasts were evaluated for the presence of capsular contracture. Patients without clinical capsular contracture, Baker I and II, were completed with therapy. Patients with clinical capsular contracture, either Baker III or IV, were treated with an additional three months of Singulair therapy as prescribed with the continuation of implant displacement therapy protocol. If patients declined to take Singulair or had side effects from the medication, implant displacement therapy protocol was continued and patients were offered 800 units-1000 units of Vitamin E daily in lieu of Singulair.

Patients that were administered Accolate were treated according to the method described in FIGS. 1 and 2 of the present disclosure. First, patients were evaluated clinically to see if they were a candidate for breast augmentation with physical examination and medical history. The medical history review included discussion and review of liver health, current medications, and potential contraindications or drug interactions with leukotriene inhibitors. Patients were then provided an informed consent for the use of Accolate (Zafirlukast), 20 mg twice daily. Patients were counseled to take the medication at least one hour before meals. The informed consent reviews the potential benefits and risks of this medication which is taken as an off-label indication. Breast augmentation was performed with either smooth or textured silicone or saline implants. On the day following surgery, Accolate therapy was initiated, 20 mg BID. In the first week following surgery, the implant displacement therapy protocol was begun for patients with smooth surface silicone implants. The implant displacement therapy protocol may also be performed, if indicated, for patients with mildly textured breast implants, but not with moderately textured or highly textured devices. Monitoring for side effects from Accolate was conducted by educating patients as to the common side effects and discussing with patients noted side effects. Accolate can be discontinued if the side effects are significant.

At thirty days postoperatively, blood testing was performed, with a measurement of transaminase levels and liver function studies. The softness of the breast implants as well as the implant movement and position was evaluated to determine if capsular contracture was present. Patients with normal liver function studies were provided two more months of Accolate therapy. At the completion of this, two additional months of treatment, the breasts were evaluated for the presence of capsular contracture. Patients without clinical capsular contracture, Baker I and II, were completed with therapy. Patients with clinical capsular contracture, either Baker III or IV, underwent repeat liver function studies. If transaminase levels were within normal limits, an additional three months of Accolate therapy was prescribed with the continuation of breast implant displacement therapy.

If liver function studies were abnormal and transaminase levels were elevated at any time in the treatment period, Accolate therapy was immediately discontinued and repeat liver function studies were performed every 14 days until normal levels were reached. If applicable, breast implant displacement therapy was continued and patients were offered 800 units-1000 units of Vitamin E daily in lieu of Accolate. Patients undergoing treatment with Accolate were monitored with a blood testing program. Following thirty days of treatment with Accolate, patients underwent liver function studies with evaluation of transaminase enzymes, including SGOT and SGPT, or ALT and AST. Normal ranges of enzyme levels were required to continue Accolate therapy.

Patients treated with leukotriene inhibitors began medication the day following surgery. Patients with a history of hepatitis or liver disease were excluded. Patients were treated with the standard dosing for each medication, recommended by the manufacturer for on-label use. Singulair 10 mg/day or Accolate 20 mg/bid were utilized. Patient compliance with the recommended dosing was encouraged. Patients were asked to report perceived side effects of the medications, and medications were discontinued at any time the patient felt that the side effects were significant.

Within the first week following surgery, the exact time determined clinically by the degree of postoperative edema experienced by the patient, the implant displacement therapy protocol and leukotriene inhibitor therapy was initiated by the patient. Patients were instructed in the implant displacement techniques and were provided with prescriptions for either Montelukast (Singulair) 10 mg to be taken daily or Zifurlukast (Accolate) 20 mg to be taken twice daily. Medications were taken approximately 1 hour before meals. Implant displacement therapy and leukotriene inhibitor therapy were initiated and patients were seen at multiple time frames following surgery to be evaluated. Compliance and mastery of the implant displacement therapy protocol was evaluated and adjustments in implant displacement technique were made as necessary. These postoperative evaluations include the following time frames: one day, one week, three to four weeks, three months, six months, and one year.

Postoperative followup appointments included an evaluation of breast implant position, softness and compliance, as well as mobility. A Baker scale is used to rate any capsular contracture present. When clinical capsular contracture is present, Baker III and IV capsules, patients are treated for up to six months with leukotriene receptor inhibitors and implant displacement techniques administered according to the implant displacement therapy protocol described herein.

All patients receiving Accolate therapy underwent liver function studies four weeks following the initiation of Accolate therapy. Elevation of transaminases resulted in discontinuation of the medication. Follow-up liver function studies were performed at two week intervals, until transaminases normalized. Patients who demonstrated Baker III or IV capsular contractures at 3 month follow-up were offered three additional months of either Singulair or Accolate therapy. Liver function studies were repeated after three months of Accolate therapy for patients choosing to continue Accolate for a six month course.

All patients were evaluated at frequent follow-up appointments, including early postoperative visits, one month, three months, six months, and one year postoperatively. Capsular contracture was evaluated by the Baker scale. Patients with grade III or IV capsular contractures were considered clinically encapsulated. Statistical comparison of the groups was performed with the Barnard's exact test. Confidence intervals for each of the groups shown in tables 3 and 4 were calculated using Jeffreys confidence interval analysis.

Table 1 shows the groups of consecutive patients who completed the study protocol with one-year follow-up. A high degree of compliance with the study was achieved with 84.8% of Accolate treated patients, 82.2% of Singulair treated patients, and 79.4% of no leukotriene inhibitor treated patients completing the one-year follow-up. Of the patients evaluated, 72% underwent a periareolar approach, while 28% chose an inframammary incision. There were no differences in the percentage of patients choosing a particular incision type between the groups. For patients offered leukotriene therapy following breast augmentation, twenty-two patients declined to participate and were not included in the study. For patients treated with Singulair, 2.5% of patients claimed to discontinue the medication because of side effects or cost. The percentage of patients discontinuing Accolate was 6.2% for minor side effects or cost. Three patients out of 520 treated with Accolate therapy (0.58%) demonstrated mild elevation of transaminases and discontinued the medication. Transaminases returned to normal within two weeks following the discontinuing the medication for two patients and within four weeks for one patient. A summary of the most common side effects reported by patients for each leukotriene inhibitor is listed in Table 2.

TABLE 1

Numbers of Patients undergoing Primary Silicone Gel Breast Augmentation Treated with or without Leukotriene Inhibitors

| | |
|---|---|
| No Leukotriene Inihbitors | 355 (31.6%) |
| Singulair Therapy | 247 (22.0%) |
| Accolate Therapy | 520 (46.3%) |

TABLE 2

Common Side Effects Reported by Patients Taking Leukotriene Inhibitor Medications Following Primary Silicone Gel Breast Augmentation

| | |
|---|---|
| Singulair | headache, GI symptoms, fatigue, rash |
| Accolate | headache, mood changes, insomnia, vivid dreams, rash, muscle pain, GI symptoms |

The rate of capsular contracture for patients undergoing primary silicone gel breast augmentation with or without leukotriene inhibitor therapy is listed in Table 3. Women undergoing breast augmentation followed by three months of Accolate therapy demonstrated capsular contracture rates significantly lower than women not treated with leukotriene inhibitors postoperatively (p<0.05). Patients treated with Singulair therapy also showed capsular contracture rates lower than patients not treated with leukotriene inhibitors. For patients treated with Singulair for three months, two patients developed grade III/IV capsular contractures which improved (to grade II) with an additional three months of therapy. For patients treated with Accolate for three months, five patients demonstrating grade III or IV capsular contractures at three months postoperatively improved with an additional three months of therapy (to grade II).

TABLE 3

Percentage of Patients Demonstrating Capsular Contracture at One Year Following Primary Silicone Gel Breast Augmentation

| | % of Patients with Capsular Contracture | 95% confidence interval (Jeffreys) |
|---|---|---|
| No Leukotriene Inhibitor | 5.02% | (0.0284, 0.0819) |
| Singulair Therapy | 3.27% | (0.0126, 0.0701) |
| Accolate Therapy | 2.19%* | (0.0101, 0.0398) |

*p < 0.05

Table 4 demonstrates the distribution of capsular contractures based on incision location for each of the groups studied. All groups of patients demonstrated a greater percentage of capsular contractures with the periareolar incision compared to the inframammary incision. For patients treated with Accolate, the capsular contracture rates were similar comparing both incision locations. However, there were no statistically significant differences between the groups based on incision location.

TABLE 4

Number and Percentage of Patients Demonstrating Capsular Contracture by Incision Location at One Year Following Silicone Gel Breast Augmentation

| | Periareolar | Inframammary | Total |
|---|---|---|---|
| No Leukotriene Inhibitor | 11/189 (5.82%) | 2/70 (2.86%) | 13/259 (5.02%) |
| Singulair Therapy | 4/105 (3.81%) | 1/48 (2.08%) | 5/153 (3.27%) |
| Accolate Therapy | 6/2560 (2.38%) | 2/115 (1.74%) | 8/375 (2.19%) |

The results of this study demonstrated that Accolate and Singulair used for three months postoperatively following primary silicone gel breast augmentation with smooth surface gel implants, in combination with the presently disclosed implant displacement therapy protocol, was associated with significantly lower capsular contracture rates at one year follow-up compared to patients not treated with a leukotriene inhibitor and implant displacement postoperatively. This demonstrates that prophylactic leukotriene inhibitor therapy utilized for patients undergoing primary silicone gel breast augmentation, in combination with the presently disclosed implant displacement therapy protocol, is correlated to a lower capsular contracture rate at one year follow-up.

In this study, 0.58% (3/520) of patients treated with Accolate showed elevated transaminases at 30 days of treatment, with complete normalization of transaminases after discontinuation of the medication and retesting. There were no known long term complications or injuries with the use of leukotriene inhibitors.

The results of this study suggest that Accolate and Singulair can be given prophylactically in a safe and effective manner according to the presently disclosed method.

A particular subgroup of patients may benefit from Accolate or Singulair therapy. Since studies suggest that periareolar incisions are associated with a higher incidence of capsular contracture, patients who undergo this incision may in particular benefit from prophylactic therapy and can be counseled in this regard. This is also supported by data in the current study, (Table 4), where patients undergoing periareolar augmentation without a leukotriene inhibitor had a capsular contracture rate of 5.82%, while patients having a periareolar augmentation with postoperative Accolate had a capsular contracture rate of 2.31%.

The current study demonstrates that Accolate and Singulair therapy reduced capsular contracture formation when used in the first three months following breast augmentation with smooth surface silicone gel implants, when administered according to the presently disclosed method. In particular, the addition of Accolate reduced the encapsulation risk by over 50%. The medication was tolerated well by almost 95% of patients, with no irreversible side effects noted in the study.

EXAMPLE 2

Treatment and Prevention of Capsular Contracture in Patients Undergoing Capsulectomy and Silicone Breast Implant Replacement Surgery The study was performed with patients undergoing primary capsulectomy and silicone implant replacement for grade III and IV capsular contracture according to the methods depicted in FIGS. 3 and 4 of the present disclosure. Patients had a history of either primary smooth silicone breast augmentation or primary smooth silicone augmentation-mastopexy performed in a subpectoral position. Patients with a history of subglandular breast augmentation or those who underwent concurrent mastopexy revision or replacement with textured silicone breast implants were not included in the study. Enrolled patients underwent surgery with either an inframammary or periareolar incision.

One group of patients underwent capsulectomy and implant replacement without the use of leukotriene inhibitors. Another group of patients agreed to the off-label use of zafirlukast (Accolate; AstraZeneca Pharmaceuticals, Wilmington, Del.) and were treated beginning the day following the capsulectomy and implant replacement procedure. All patients were between the ages of 22 and 60 years of age and consented to the use of Mentor Memory Gel silicone gel breast implants with a smooth surface (Mentor Worldwide, Irvine, Calif.) and the off-label use of triple-antibiotic irrigation containing povidone-iodine (Betadine; Purdue Frederick Co., Norwalk, Conn.). In addition, a detailed informed consent was provided for the off-label use of Accolate. All patients were adequately informed of the risks, potential unknown benefits, cost, and potential side effects of leukotriene therapy with both verbal and written consent. Patients were informed that taking Accolate was voluntary and that they could discontinue this medication at any time for any reason. In particular, patients were counseled on the potential significant risks of Accolate, including the uncommon risk of chemical hepatitis, liver failure, and even death, all of which were reported in Accolate U.S. Food and Drug Administration postapproval studies for the treatment of asthma.

Patients undergoing capsulectory and re-augmentation were treated with the incision initially used by the original surgeon, with either an inframmary or periareolar approach. All patients were surgically treated with complete periprosthetic capsulectomy. Patients were also treated with preoperative intravenous antibiotics, either a 1-g dose of cephazolin or 600 mg of clindamycin, selected based on allergy profiles. Before insertion of implants, triple-antibiotic irrigation [50,000 U of bacitracin, 1 g of Ancef (GlaxoSmithKline, Middlesex, United Kingdom), and 80 mg of gentamicin] with the addition of 50 ml of povidone-iodine in 500 ml of normal saline was used.

Hemovac ⅛ inch drains (Medline Industries, Rialto, Calif.) were used on all breasts receiving capsulectomy. All implants were placed with powder-free glove changes and inserted through a skin barrier/nipple shield using Tegaderm (3M, St. Paul, Minn.) dressings. Drains were left in place until drainage from one breast reached 30 ml/24 hrs, or 60 ml/24 hrs if both breasts were treated. The implant displacement therapy protocol was initiated two days after drains were removed.

Patients were treated with Accolate 20 mg twice daily, beginning the day after surgery. Patients with a history of hepatitis or liver disease were excluded. Patient compliance with the recommended dosage was encouraged, but patients were advised that they could discontinue the medication at any time that they experienced significant side effects. All patients receiving Accolate therapy underwent liver function studies 4 weeks after the initiation of Accolate therapy. Elevation of transaminases resulted in discontinuation of the medication. Follow-up liver function studies were performed at 2-week intervals, until transaminases normalized. Patients who demonstrated Baker grade III or IV capsular contractures at 3-month follow-up were offered 3 additional months of Accolate therapy. Liver function studies were repeated after 3 months of Accolate therapy for patients choosing to continue Accolate for a 6-month course.

All patients were evaluated at frequent follow-up appointments, including early postoperative visits, 1 month, 3 months, 6 months, and 1 year postoperatively. Capsular contracture was evaluated by the Baker scale. Patients with grade III or IV capsular contractures were considered as having clinical capsular contracture. Each patient was considered based on the number of their breasts associated with clinical capsular contracture ranging from none to two breasts. For patients with bilateral capsular contracture of different grades, each breast was evaluated independently within the same patient, with preoperative and postoperative evaluation and statistical analysis. Statistical comparison of the groups was performed with the Barnard exact test.

A total of 447 consecutive patients were evaluated during the study period. A first group of 168 consecutive patients with encapsulated breast implants were studied and no leukotriene inhibitor therapy was offered postoperatively. This included 55 patients with bilateral capsular contracture. There were 223 breasts demonstrating capsular contracture among the patients in this group. A second group of 279 consecutive patients with encapsulated breast implants were studied and treated with Accolate, including 87 patients with bilateral capsular contracture. There were 366 breasts with capsular contracture among patients in this group. Two patients demonstrated mild elevation of transaminases when evaluated at one month postoperatively. These two patients discontinued the use of Accolate and demonstrated normalization of transaminase levels within two weeks of discontinuing therapy. Twelve patients discontinued the use of Accolate voluntarily based on cost or minor side effects and were excluded from the study. Table 5 shows the distribution of patients in each group by the number of breasts which demonstrated capsular contracture.

There was a high rate of compliance of patients in this study, with 81.1 of no leukotriene inhibitor treatment patients, and 77.2% of Accolate therapy patients completing the one-year follow-up.

TABLE 5

The number of breasts demonstrating capsular contracture among patients preoperatively by patient group.

| Group | Grade III | Grade IV | Total Breasts |
|---|---|---|---|
| No Leukotriene Inhibitor | 96 | 127 | 223 |
| Accolate Therapy | 172 | 194 | 366 |

Table 6 shows the capsular contracture rates at one year with no leukotriene inhibitor, as percentages, for patients presenting with either grade III or grade IV capsular contractures preoperatively. Patients presenting with grade III contractures were more likely to recur as a grade III versus a grade IV. Patients presenting with a grade IV contracture were more likely to recur as a grade IV. The recurrence rate of capsular contracture was higher for patients presenting with grade IV contractures compared to grade III contractures.

TABLE 6

Number and Percent of Breasts with Capsular Contracture One-Year Following no Leukotriene Receptor Inhibitor Therapy

| Preoperative Capsular Contracture Grade | Postoperative Capsular Contracture Grade | | |
|---|---|---|---|
| | Grade III | Grade IV | Total |
| Grade III (96) | 7 (7.3%) | 4 (4.2%) | 11 (11.5%) |
| Grade IV (127) | 7 (5.5%) | 18 (14.2%) | 25 (19.7%) |
| Total III/IV (223) | 14 (6.3%) | 22 (9.9%) | 36 (16.1%) |

Table 7 shows the capsular contracture rates at one year with post-operative Accolate therapy, as percentages, for patients with grade III, grade IV and the total of capsular contractures (grades III and IV). There was a statistically significant ($p<0.01$) decrease in capsular contracture rates for total capsular contractures (grades III+IV) compared to patients not treated with a leukotriene inhibitor. There was also a statistically significant ($p<0.05$) decrease in capsular contracture recurrence in patients presenting specifically with a grade IV capsular contracture preoperatively.

TABLE 7

Number and Percent of Breasts with Capsular Contracture One-Year Following Accolate Therapy.

| Preoperative Capsular Contracture Grade | Postoperative Capsular Contracture Grade | | |
|---|---|---|---|
| | Grade III | Grade IV | Total |
| Grade III (172) | 7 (4.1%) | 2 (1.2%) | 9 (5.3%) |
| Grade IV (194) | 15 (7.8%) | 5 (2.6%) | 20 (10.3%)* |
| Total III/IV (366) | 22 (6.0%) | 7 (1.9%) | 29 (7.9%)** |

*$p < 0.05$
**$p < 0.01$

Table 8 demonstrates the distribution of incision location among patients in the groups studied. There were no differences between the no leukotriene group and Accolate group in the distribution of patients receiving each incision.

TABLE 8

Percentage of Patients Demonstrating Capsular Contracture by Incision Location at 1 Year after Revisional Capsulectomy and Implant Exchange

|  | Inframammary | Periareolar |
|---|---|---|
| No Leukotriene Receptor Inhibitor | 60.7 | 39.3 |
| Accolate Therapy | 57.7 | 42.3 |

This study demonstrates that patients treated with Accolate therapy for at least three months after revisional surgery for capsular contracture, in combination with the presently disclosed implant displacement therapy protocol, have statistically significantly lower capsular contracture rates at one year than patients not treated with a leukotriene inhibitor nor receiving the implant displacement therapy protocol. Patients receiving Accolate therapy had a significantly lower capsular contracture recurrence rate, ($p<0.01$), than for patients not taking Accolate therapy. In addition, patients presenting with grade IV capsular contractures had statistically lower recurrence rates of capsular contracture than patients not treated with Accolate ($p<0.05$). This is the first report demonstrating that Accolate taken in the perioperative period following surgical treatment, and in combination with the presently disclosed implant displacement therapy is effective in reducing the recurrence of capsular contracture.

Statements of the Disclosure Include

Statement 1: A method of treating or preventing capsular contracture in a patient resulting from surgical insertion of a silicone breast implant in a surgically created implant pocket, the method comprising: administering to the patient a therapeutically effective amount of a leukotriene receptor antagonist prior to the formation of a capsular contracture in the patient; and administering a therapeutically effective amount of displacement of the breast implant within the surgically created implant pocket, the therapeutically effective amount of displacement of the breast implant being administered post-surgically but prior to the formation of a capsular contracture in the patient.

Statement 2: A method according to Statement 1, wherein the therapeutically effective amount of a leukotriene receptor antagonist is administered perioperatively and continued for at least three months following surgical insertion of the silicone breast implant in the surgically created implant pocket.

Statement 3: A method according to Statement 1 or Statement 2, wherein the leukotriene receptor antagonist is selected from the group consisting of montelukast and zafirlukast.

Statement 4: A method according to any one of the preceding Statements 1-3, wherein the leukotriene receptor antagonist is zafirlukast and the therapeutically effective amount is 20 mg/bid administered orally.

Statement 5: A method according to any one of the preceding Statements 1-4, wherein the leukotriene receptor antagonist is montelukast and the therapeutically effective amount is 10 mg/day administered orally.

Statement 6: A method according to any one of the preceding Statements 1-5, wherein the therapeutically effective amount of displacement comprises one or more selected from the group consisting of upward displacement, upward and downward displacement, and inward-outward displacement or outward-inward displacement, the displacement administered such that the displacement comprises at least ten repetitions administered at least three times daily.

Statement 7: A method according to any one of the preceding Statements 1-5, wherein the therapeutically effective amount of displacement comprises displacing the implant from its resting position in the implant pocket in an upward direction and extending to the upper-most limit of implant movement or to the limits of the surgically-created pocket.

Statement 8: A method according to any one of the preceding Statements 1-5, wherein the therapeutically effective amount of displacement comprises displacing the implant in both an upward and downward direction, the displacement administered such that the displacement comprises at least ten repetitions administered at least three times daily.

Statement 9: A method according to any one of the preceding Statements 1-5, wherein the therapeutically effective amount of displacement comprises displacing the implant from an inner portion of a breast to an outer portion of the breast or displacing the implant from the outer portion of the breast to the inner portion, the displacement administered such that the displacement comprises at least ten repetitions administered at least three times daily.

Statement 10: A method according to any one of the preceding Statements 1-9, further comprising: monitoring transaminase levels in the blood of the patient; and determining whether to continue leukotriene receptor antagonist administration based on the monitoring of transaminase levels.

Statement 11: A method according to any one of the preceding Statements 1-5, wherein administering to the patient a therapeutically effective amount of a leukotriene receptor antagonist comprises administration until either: the patient exhibits a Baker I or Baker II grade breast for at least three months following insertion of a silicone implant in a surgically created implant pocket in that breast; or the patient exhibits blood levels of transaminase that are elevated beyond safe limits.

Statement 12: A method according to any one of the preceding Statements 1-11, wherein the silicone implant is a smooth silicone implant.

Statement 13: A method according to any one of the preceding Statements 1-12, further comprising administering to the patient antibiotic-betadine irrigation.

Statement 14: A method of treating or preventing recurrence of capsular contracture in a patient undergoing capsulectomy and silicone breast implant replacement surgery, the method comprising: perioperative administration to the patient of a therapeutically effective amount of a leukotriene receptor antagonist; and administering a therapeutically effective amount of displacement of the breast implant within the surgically created implant pocket, the therapeutically effective amount of displacement of the breast implant being administered post-surgically but prior to the recurrence of a capsular contracture in the patient.

Statement 15: A method according to Statement 14, wherein the therapeutically effective amount of a leukotriene receptor antagonist is administered for at least three months following surgical insertion of the silicone breast implant in the surgically created implant pocket.

Statement 16: A method according to Statement 14 or Statement 15, wherein the leukotriene receptor antagonist is selected from the group consisting of montelukast and zafirlukast.

Statement 17: A method according to any one of the preceding Statements 14-16, wherein the leukotriene receptor antagonist is zafirlukast and the therapeutically effective amount is 20 mg/bid administered orally.

Statement 18: A method according to any one of the preceding Statements 14-16, wherein the leukotriene receptor antagonist is montelukast and the therapeutically effective amount is 10 mg/day administered orally.

Statement 19: A method according to any one of the preceding Statements 14-18, wherein the therapeutically effective amount of displacement comprises one or more selected from the group consisting of upward displacement, upward and downward displacement, and inward-outward or outward-inward displacement, the displacement administered such that the displacement comprises at least ten repetitions administered at least three times daily.

Statement 20: A method according to any one of the preceding Statements 14-18, wherein the therapeutically effective amount of displacement comprises displacing the implant from its resting position in the implant pocket in an upward direction and extending to the upper-most limit of the surgically created pocket.

Statement 21: A method according to any one of the preceding Statements 14-18, wherein the therapeutically effective amount of displacement comprises displacing the implant in both an upward and downward direction, the displacement administered such that the displacement comprises at least ten repetitions administered at least three times daily.

Statement 22: A method according to any one of the preceding Statements 14-18, wherein the therapeutically effective amount of displacement comprises displacing the implant from the inner portion of a breast to an outer portion of the breast, or the displacement from the outer portion of the breast to the inner portion of the breast, the displacement administered such that the displacement comprises at least ten repetitions administered at least three times daily.

Statement 23: A method according to any one of the preceding Statements 14-22, further comprising: monitoring transaminase levels in the blood of the patient; and determining whether to continue leukotriene receptor antagonist administration based on the monitoring of transaminase levels.

Statement 24: A method according to any one of the preceding Statements 14-23, wherein administering to the patient a therapeutically effective amount of a leukotriene receptor antagonist comprises administration until either: the patient exhibits a Baker I or Baker II grade breast for at least three months following insertion of a silicone implant in a surgically created implant pocket in that breast; or the patient exhibits blood levels of transaminase that are elevated beyond safe limits.

Statement 25: A method according to any one of the preceding Statements 14-24, wherein the silicone implant is a smooth silicone implant.

Statement 26: A method according to any one of the preceding Statements 14-25, further comprising administering to the patient antibiotic-betadine irrigation.

Statement 27: A method of treating capsular contracture associated with a silicone breast implant in a patient, the method comprising: removing the silicone implant from a surgically created implant pocket in the patient; performing a capsulectomy to remove the scar tissue surrounding the implant pocket; inserting a replacement silicone implant into the implant pocket; administering to the patient a therapeutically effective amount of a leukotriene receptor antagonist prior to the formation of a capsular contracture associated with the replacement silicone implant in the patient; and performing displacement of the replacement silicone implant within the surgically created implant pocket, the displacement of the replacement breast implant performed post-surgically but prior to the formation of a capsular contracture in the patient associated with the replacement silicone implant.

Statement 28: A method according to Statement 27, wherein the therapeutically effective amount of a leukotriene receptor antagonist is administered perioperatively and continued for at least three months following surgical insertion of the replacement silicone implant in the implant pocket.

Statement 29: A method according to Statement 27 or Statement 28, wherein the leukotriene receptor antagonist is selected from the group consisting of montelukast and zafirlukast.

Statement 30: A method according to any one of the preceding Statements 27-29, wherein the leukotriene receptor antagonist is zafirlukast and the therapeutically effective amount is 20 mg/bid administered orally.

Statement 31: A method according to any one of the preceding Statements 27-29, wherein the leukotriene receptor antagonist is montelukast and the therapeutically effective amount is 10 mg/day administered orally.

Statement 32: A method according to any one of the preceding Statements 27-31, wherein the therapeutically effective amount of displacement comprises one or more selected from the group consisting of upward displacement, upward and downward displacement, and inward-outward and outward-inward displacement, the displacement administered such that the displacement comprises at least ten repetitions administered at least three times daily.

Statement 33: A method according to any one of the preceding Statements 27-31, wherein the therapeutically effective amount of displacement comprises displacing the implant from its resting position in the implant pocket in an upward direction and extending to the upper-most limit of implant movement or the limit of surgical pocket creation.

Statement 34: A method according to any one of the preceding Statements 27-31, wherein the therapeutically effective amount of displacement comprises displacing the implant in both an upward and downward direction, the displacement administered such that the displacement comprises at least ten repetitions administered at least three times daily.

Statement 35: A method according to any one of the preceding Statements 27-31, wherein the therapeutically effective amount of displacement comprises displacing the implant from an inner portion of a breast to an outer portion of the breast or the displacement from the outer portion of the breast to the inner portion of the breast, the displacement administered such that the displacement comprises at least ten repetitions administered at least three times daily.

Statement 36: A method according to any one of the preceding Statements 27-35, further comprising: monitoring transaminase levels in the blood of the patient; and determining whether to continue leukotriene receptor antagonist administration based on the monitoring of transaminase levels.

Statement 37: A method according to any one of the preceding Statements 27-36, wherein administering to the patient a therapeutically effective amount of a leukotriene receptor antagonist comprises administration until either: the patient exhibits a Baker I or Baker II grade breast for at least three months following insertion of a silicone implant in a surgically created implant pocket in that breast; or the patient exhibits blood levels of transaminase that are elevated beyond safe limits.

Statement 38: A method according to any one of the preceding Statements 27-37, wherein the silicone implant is a smooth silicone implant.

Statement 39: A method according to any one of the preceding Statements 27-38, further comprising administering to the patient triple antibiotic-betadine irrigation.

Statement 40: A method of treating recurrence of capsular contracture in a patient following silicone implant replacement for grade III or IV capsular contracture, the method comprising: removing the silicone implant from a surgically created implant pocket in the patient; performing a capsulectomy to remove the scar tissue surrounding the implant pocket; inserting a replacement silicone implant into the implant pocket; administering to the patient a therapeutically effective amount of a leukotriene receptor antagonist prior to the formation of a capsular contracture associated with the replacement silicone implant in the patient; and causing the displacement of the replacement silicone implant within the surgically created implant pocket, the therapeutically effective amount of displacement of the breast implant being administered post-surgically but prior to the formation of a capsular contracture in the patient associated with the replacement silicone implant.

Statement 41: A method according to Statement 40, wherein the therapeutically effective amount of a leukotriene receptor antagonist is administered perioperatively and continued for at least 3 months following surgical insertion of the replacement silicone implant in the implant pocket.

Statement 42: A method according to Statement 40 or Statement 41, wherein the leukotriene receptor antagonist is selected from the group consisting of montelukast and zafirlukast.

Statement 43: A method according to any one of the preceding Statements 40-42, wherein the leukotriene receptor antagonist is zafirlukast and the therapeutically effective amount is 20 mg/bid administered orally.

Statement 44: A method according to any one of the preceding Statements 40-42, wherein the leukotriene receptor antagonist is montelukast and the therapeutically effective amount is 10 mg/day administered orally.

Statement 45: A method according to any one of the preceding Statements 40-44, wherein the therapeutically effective amount of displacement comprises one or more selected from the group consisting of upward displacement, upward and downward displacement, and inward-outward displacement or outward-inward displacement, the displacement administered such that the displacement comprises at least ten repetitions administered at least three times daily.

Statement 46: A method according to any one of the preceding Statements 40-44, wherein the therapeutically effective amount of displacement comprises displacing the implant from its resting position in the implant pocket in an upward direction and extending to the upper-most limit of implant movement or the limits of the surgically created pocket.

Statement 47: A method according to any one of the preceding Statements 40-44, wherein the therapeutically effective amount of displacement comprises displacing the implant in both an upward and downward direction, the displacement administered such that the displacement comprises at least ten repetitions administered at least three times daily.

Statement 48: A method according to any one of the preceding Statements 40-44, wherein the therapeutically effective amount of displacement comprises displacing the implant from an inner portion of a breast to an outer portion of the breast or the outer portion of the breast to the inner portion of the breast, the displacement administered such that the displacement comprises at least ten repetitions administered at least three times daily.

Statement 49: A method according to any one of the preceding Statements 40-48, further comprising: monitoring transaminase levels in the blood of the patient; and determining whether to continue leukotriene receptor antagonist administration based on the monitoring of transaminase levels.

Statement 50: A method according to any one of the preceding Statements 40-49, wherein administering to the patient a therapeutically effective amount of a leukotriene receptor antagonist comprises administration until either: the patient exhibits a Baker I or Baker II grade breast for at least three months following insertion of a silicone implant in a surgically created implant pocket in that breast; or the patient exhibits blood levels of transaminase that are elevated beyond safe limits.

Statement 51: A method according to any one of the preceding Statements 40-50, wherein the silicone implant is a smooth silicone implant.

Statement 52: A method according to any one of the preceding Statements 40-51, further comprising administering to the patient antibiotic-betadine irrigation.

Statement 53: A method of treating capsular contracture in a patient undergoing capsulectomy and silicone breast implant replacement surgery, the method comprising: perioperative administration to the patient of a therapeutically effective amount of a leukotriene receptor antagonist, the administration of a therapeutically effective amount of a leukotriene receptor antagonist occurring prior to the formation of capsular contracture in the patient as a result of an insertion of the replacement implant into a surgically created implant pocket.

Statement 54: A method according to statement 53, further comprising administering a therapeutically effective amount of displacement of the breast implant within the surgically created implant pocket, the therapeutically effective amount of displacement of the breast implant being administered post-surgically but prior to the recurrence of a capsular contracture in the patient.

Statement 55: A method according to Statement 53 or Statement 54, wherein the therapeutically effective amount of a leukotriene receptor antagonist is administered for at least three months following surgical insertion of the silicone breast implant in the surgically created implant pocket.

Statement 56: A method according to any one of the preceding Statements 53-55, wherein the leukotriene receptor antagonist is selected from the group consisting of montelukast and zafirlukast.

Statement 57: A method according to any one of the preceding Statements 53-56, wherein the leukotriene receptor antagonist is zafirlukast and the therapeutically effective amount is 20 mg/bid administered orally.

Statement 58: A method according to any one of the preceding Statements 53-56, wherein the leukotriene receptor antagonist is montelukast and the therapeutically effective amount is 10 mg/day administered orally.

Statement 59: A method according to any one of the preceding Statements 53-58, wherein the therapeutically effective amount of displacement comprises one or more selected from the group consisting of upward displacement, upward and downward displacement, and inward-outward or outward-inward displacement, the displacement administered such that the displacement comprises at least ten repetitions administered at least three times daily.

Statement 60: A method according to any one of the preceding Statements 53-58, wherein the therapeutically effective amount of displacement comprises displacing the implant from its resting position in the implant pocket in an upward direction and extending to the upper-most limit of the surgically created pocket.

Statement 61: A method according to any one of the preceding Statements 53-58, wherein the therapeutically effective amount of displacement comprises displacing the implant in both an upward and downward direction, the displacement administered such that the displacement comprises at least ten repetitions administered at least three times daily.

Statement 62: A method according to any one of the preceding Statements 53-58, wherein the therapeutically effective amount of displacement comprises displacing the implant from the inner portion of a breast to an outer portion of the breast, or the displacement from the outer portion of the breast to the inner portion of the breast, the displacement administered such that the displacement comprises at least ten repetitions administered at least three times daily.

Statement 63: A method according to any one of the preceding Statements 53-62, further comprising: monitoring transaminase levels in the blood of the patient; and determining whether to continue leukotriene receptor antagonist administration based on the monitoring of transaminase levels.

Statement 64: A method according to any one of the preceding Statements 53-63, wherein administering to the patient a therapeutically effective amount of a leukotriene receptor antagonist comprises administration until either: the patient exhibits a Baker I or Baker II grade breast for at least three months following insertion of a silicone implant in a surgically created implant pocket in that breast; or the patient exhibits blood levels of transaminase that are elevated beyond safe limits.

Statement 65: A method according to any one of the preceding Statements 53-64, wherein the silicone implant is a smooth silicone implant.

Statement 66: A method according to any one of the preceding Statements 53-65, further comprising administering to the patient antibiotic-betadine irrigation.

What is claimed is:

1. A method of treating or preventing capsular contracture in a patient resulting from surgical insertion of a silicone breast implant in a surgically created implant pocket, the method comprising:
   administering to the patient a therapeutically effective amount of a leukotriene receptor antagonist prior to the formation of a capsular contracture in the patient, wherein the therapeutically effective amount of a leukotriene receptor antagonist is administered perioperatively and for at least three months following surgical insertion of the silicone breast implant in the surgically created implant pocket; and
   administering a therapeutically effective amount of displacement of the breast implant within the surgically created implant pocket, the therapeutically effective amount of displacement of the breast implant being administered post-surgically but prior to the formation of a capsular contracture in the patient;
   wherein the therapeutically effective amount of displacement of the breast implant is administered as a combination therapy in combination with the therapeutically effective amount of a leukotriene receptor antagonist during at least a portion of the three months following surgical insertion of the silicone breast implant in the surgically created implant pocket that the therapeutically effective amount of a leukotriene receptor antagonist is administered to the patient.

2. The method according to claim 1, wherein the leukotriene receptor antagonist is selected from the group consisting of montelukast and zafirlukast.

3. The method according to claim 2, wherein the leukotriene receptor antagonist is zafirlukast and the therapeutically effective amount is 20 mg/bid administered orally.

4. The method according to claim 2, wherein the leukotriene receptor antagonist is montelukast and the therapeutically effective amount is 10 mg/day administered orally.

5. The method according to claim 1, wherein the therapeutically effective amount of displacement comprises one or more selected from the group consisting of upward displacement, upward and downward displacement, and inward-outward displacement or outward-inward displacement, the displacement administered such that the displacement comprises at least ten repetitions administered at least three times daily.

6. The method according to claim 1, wherein the therapeutically effective amount of displacement comprises displacing the implant from its resting position in the implant pocket in an upward direction and extending to the upper-most limit of implant movement or to the limits of the surgically-created pocket.

7. The method according to claim 1, wherein the therapeutically effective amount of displacement comprises displacing the implant in both an upward and downward direction, the displacement administered such that the displacement comprises at least ten repetitions administered at least three times daily.

8. The method according to claim 1, wherein the therapeutically effective amount of displacement comprises displacing the implant from an inner portion of a breast to an outer portion of the breast or displacing the implant from the outer portion of the breast to the inner portion, the displacement administered such that the displacement comprises at least ten repetitions administered at least three times daily.

9. The method according to claim 1, further comprising:
   monitoring transaminase levels in the blood of the patient; and
   determining whether to continue leukotriene receptor antagonist administration based on the monitoring of transaminase levels.

10. The method according to claim 1, wherein administering to the patient a therapeutically effective amount of a leukotriene receptor antagonist comprises administration until either:
   the patient exhibits a Baker I or Baker II grade breast for at least three months following insertion of a silicone implant in a surgically created implant pocket in that breast; or
   the patient exhibits blood levels of transaminase that are elevated beyond safe limits.

11. A method of treating or preventing recurrence of capsular contracture in a patient undergoing capsulectomy and silicone breast implant replacement surgery, the method comprising:
   administering to the patient a therapeutically effective amount of a leukotriene receptor antagonist, wherein the therapeutically effective amount of a leukotriene receptor antagonist is administered perioperatively and for at least three months following silicone breast implant replacement surgery; and administering a therapeutically effective amount of displacement of the breast implant within the surgically created implant pocket, the therapeutically effective amount of displacement of the breast implant being administered post-surgically but prior to the recurrence of a capsular contracture in the patient;

wherein the therapeutically effective amount of displacement of the breast implant is administered as a combination therapy in combination with the therapeutically effective amount of a leukotriene receptor antagonist during at least a portion of the three months following silicone breast implant replacement surgery that the therapeutically effective amount of a leukotriene receptor antagonist is administered to the patient.

12. The method according to claim 11, wherein the leukotriene receptor antagonist is zafirlukast and the therapeutically effective amount is 20 mg/bid administered orally.

13. The method according to claim 11, wherein the leukotriene receptor antagonist is montelukast and the therapeutically effective amount is 10 mg/day administered orally.

14. The method according to claim 12, wherein the therapeutically effective amount of displacement comprises one or more selected from the group consisting of upward displacement, upward and downward displacement, and inward-outward or outward-inward displacement, the displacement administered such that the displacement comprises at least ten repetitions administered at least three times daily.

15. A method of treating capsular contracture associated with a silicone breast implant in a patient, the method comprising:

removing the silicone implant from a surgically created implant pocket in the patient;

performing a capsulectomy to remove the scar tissue surrounding the implant pocket;

inserting a replacement silicone implant into the implant pocket;

administering to the patient a therapeutically effective amount of a leukotriene receptor antagonist prior to the formation of a capsular contracture associated with the replacement silicone implant in the patient, wherein the therapeutically effective amount of a leukotriene receptor antagonist is administered perioperatively and for at least three months following inserting a replacement silicone implant into the implant pocket; and performing displacement of the replacement silicone implant within the surgically created implant pocket, the displacement of the replacement silicone implant being performed post-surgically but prior to the formation of a capsular contracture in the patient associated with the replacement silicone implant;

wherein the displacement of the replacement silicone implant is administered as a combination therapy in combination with the therapeutically effective amount of a leukotriene receptor antagonist during at least a portion of the three months following inserting a replacement silicone implant into the implant pocket that the therapeutically effective amount of a leukotriene receptor antagonist is administered to the patient.

16. The method according to claim 15, wherein the leukotriene receptor antagonist is either:

zafirlukast and the therapeutically effective amount is 20 mg/bid administered orally; or montelukast and the therapeutically effective amount is 10 mg/day administered orally.

17. The method according to claim 15, wherein the therapeutically effective amount of displacement comprises one or more selected from the group consisting of upward displacement, upward and downward displacement, and inward-outward and outward-inward displacement, the displacement administered such that the displacement comprises at least ten repetitions administered at least three times daily.

* * * * *